United States Patent
Low et al.

[11] Patent Number: 5,882,195
[45] Date of Patent: Mar. 16, 1999

[54] DENTAL INSTRUMENT

[76] Inventors: Gina Marie Low, 2306 Pentiquit Ave., Seaford, N.Y. 11783; Francine Martucci, 200 Woodette Dr., Dunedin, Fla. 34698

[21] Appl. No.: 50,407

[22] Filed: Mar. 30, 1998

[51] Int. Cl.[6] ............................................. A61C 1/00
[52] U.S. Cl. ................................ 433/31; 433/29; 433/80; 433/140
[58] Field of Search .................................. 433/29, 30, 31, 433/80, 81, 82, 83, 140, 215

[56] References Cited

U.S. PATENT DOCUMENTS

| | | | |
|---|---|---|---|
| D. 320,075 | 9/1991 | Berlin | D24/112 |
| 1,500,798 | 7/1924 | Campodonico | 433/31 |
| 1,647,862 | 11/1927 | Gaillard | 433/31 |
| 1,817,417 | 8/1931 | Meitzler | 433/31 |
| 1,989,162 | 1/1935 | Barr | 433/31 |
| 2,393,319 | 1/1946 | Freedman | 433/29 |
| 3,342,178 | 9/1967 | Freedman | 433/31 |
| 3,935,640 | 2/1976 | Cohan | 433/31 |
| 3,979,830 | 9/1976 | McSirley | 32/60 |
| 4,212,105 | 7/1980 | Hukuba | 433/30 |
| 4,713,002 | 12/1987 | Presser | 433/30 |
| 4,790,751 | 12/1988 | Reinhardt et al. | 433/29 |
| 4,824,367 | 4/1989 | Rosenstiel | 433/75 |
| 4,925,391 | 5/1990 | Berlin | 433/31 |
| 5,230,622 | 7/1993 | Brossoit | 433/30 |

*Primary Examiner*—Gene Mancene
*Assistant Examiner*—Pedro Philogene

[57] ABSTRACT

A dental instrument (10) has a handle (12) having a handle front (12F) and a handle rear (12R). The handle (12) further has a handle grip (12A). The dental instrument (10) further has a probe (14) which is securely attached to and extending frontwardly from the handle front (12F). The probe (14) functions to measure periodontal pockets. The probe (14) has a probe first shaft (14A) which is securely connected at a rear distal end to a front distal end of the handle front (12F). The probe first shaft (14A) is in an approximately parallel configuration to a longitudinal axis of the handle (12). The probe (14) further has a probe second shaft (14B) which is securely connected at a rear distal end at an upward obtuse angle to a front distal end of the probe first shaft (14A). The probe (14) still further has a probe point (14C) which is securely connected at a rear distal end at an approximate perpendicular downward angle to a front distal end of the probe second shaft (14B). The probe point (14C) is imprinted with indicia for indicating distance form the tip.

4 Claims, 2 Drawing Sheets

DENTAL INSTRUMENT

FIELD OF THE INVENTION

The present invention relates to medical instruments. More particularly, the present invention relates to dental tools.

DESCRIPTION OF THE PRIOR ART

Numerous innovations for dental instruments have been provided in the prior art that are described as follows. Even though these innovations may be suitable for the specific individual purposes to which they address, they differ from the present invention as hereinafter contrasted.

In U.S. Pat. No. D320,075, titled Combined Dental Mirror and Suction Instrument, invented by Goran Berlin, an ornamental design for a combined dental mirror and suction instrument, as shown and described.

The patented invention differs from the present invention because the patented invention is ornamental design for a combined dental mirror and suction instrument. The patented invention lacks an attachment for other dental instruments.

In U.S. Pat. No. 4,925,391, titled Dental Instrument, invented by Goran Berlin, a dental instrument including a shaft having firmly attached at one end thereof a mirror, which is carried by a housing provided with an inlet opening to a first internal channel which communicates with a channel provided in the shaft, this latter channel being intended for connection to a suction source. According to the invention the shaft (17) incorporates a second channel (16) having one end which opens above the mirror (2) and the other end of which is intended for connection to a pressurized-air source via a control means (23) effective to regulate the supply of pressurized air to a turbine drill, whereby the supply of pressurized air to the instrument (1) is proportional to the supply of pressurized air to the turbine drill, and whereby the pressurized air supplied to the instrument (1) is blown over the mirror (2).

The patented invention differs from the present invention because the patented invention is a combined dental mirror and suction instrument. The patented invention lacks an attachment for other dental instruments.

In U.S. Pat. No. 4,824,367, titled Dental Drill Alignment Indicator, invented by Stephen F. Rosenstiel and Edwin R. I. Deane, a dental surgery when a tooth is to be crowned, the tooth has to be prepared by cutting a taper. It has been found that for the successful mounting of a crown the taper must be much more exactly prepared than is possible using currently available equipment. The present invention allows the initial position of the axis of a cutter to be related by means of electronic "spirit levels" to a selected axis. Deviation from this axis by more than a predetermined amount is indicated by light sources which can be seen regardless of the position of a handpiece holding the cutter. By means of a code these light sources indicate how the dentist must move the cutter to return to the correct axis.

The patented invention differs from the present invention because the patented invention is a positioning device for a dental drill. The patented invention lacks features similar to the present invention.

In U.S. Pat. No. 4,790,751, titled Dental Viewing Apparatus and Method, invented by Richard A. Reinhardt and Gerald J. Tussing, to permit more effective viewing during dental surgery of diagnosis, a retractor or probe assembly includes: (1) a cylindrical stainless steel handle about 14 centimeters long and 7 millimeters in diameter to which a mirror may be mounted; and (2) a 15 millimeter long retractor or probe extending at right angles to the handle with openings in it for the passage of light and an opening near the retractor or probe for water and air. One end of the handle opposite to the retractor or probe receives an air hose, a water hose and a fiber optic bundle connected to a dental light source to supply air, water and/or light to the retractor or probe end of the handle. The retractor or probe assembly: (1) supplies light with sufficient intensity for transillumination or direct illumination of the dental root, pulp chamber, or other constricted areas in the oral cavity; and (2) in the case of a blade shaped retractor, is strong enough to permit insertion into and retraction of the gingival tissue or other oral soft tissue.

The patented invention differs from the present invention because the patented invention is a retraction tool which has an integral illumination, water and air source attached. The mirror is adjustable. The present invention is a dental tool which has a handle having a smooth flat end, and a grip area, the opposite distal end is forked having a dental tool on one fork and a dental mirror on the other.

In U.S. Pat. No. 4,713,002, titled Dental Mirror, invented by Dwight W. Presser and Joseph J Berke, an improved dental mirror or instrument of the type including an elongated handle and a disc-like mirror mounted in a frame at one end of the handle. A concave clear plastic shell is sealed relative to the mirror surface to substantially reduce, if not completely eliminate, condensation. The concave exterior surface, which is dome-like in configuration, may be comfortably and conveniently wiped on the inside cheek of the patient to assist in maintaining the surface clear and clean, and to assist in removal of debris from the mouth of the patient.

The patented invention differs from the present invention because the patented invention is an improved dental mirror with a disc-like mirror mounted in a frame at one end of the handle. A concave clear plastic shell is securely and removably attached to the mirror surface to prevent condensation. The attachment means provides for an air tight seal between the mirror surface and the cover. The patented invention lacks features similar to the present invention.

In U.S. Pat. No. 3,979,830, titled Dental Amalgam Carrier, invented by Robert C. McShirley, a dental instrument for carrying amalgam from a mixing station to a patient's tooth cavity. The instrument includes an elongated handle which is rotatably coupled to a mirror frame. This frame supports an amalgam carrying bucket and a mirror. The bucket swings away from the frame for filling, and is locked in place, adjacent to the mirror for transferring amalgam into a cavity.

The patented invention differs from the present invention because the patented invention is a dental instrument for carrying amalgam. The patented invention further includes a dental mirror which is positioned to view a cavity into which the amalgam is to be place. The patented invention lacks a forked end and provisions for the attachment of various dental instruments. The present invention is a dental tool which has a handle having a smooth flat end, and a grip area, the opposite distal end is forked having an attachment means for accepting a dental tool on one fork and an attachment means for accepting a dental mirror on the other. A series of dental tools adapted to attach to the tine of the fork.

In U.S. Pat. No. 3,935,640, titled Dental Instrument, invented by Richard Philip Cohan, a dental instrument comprising a metal shaft having a resilient extension at one end and a further functionally closely related instrument such as a periodontal probe or mirror at the other end. The resilient extension has two deformable surfaces which can be pressed against a tooth to test its mobility. The periodontal probe is color-coded, so that the depth to which the projection has been inserted into the gingival sulcus and any existing periodontal pocket is readily apparent to the dentist. The dental instrument can include a percussive hammer adjacent the resilient section.

The patented invention differs from the present invention because the patented invention is a dental instrument which has a shaft with a resilient extension on one end. The resilient extension has deformable surfaces which are used to test the mobility of a tooth. The opposite end of the shaft has a removable attachment means which accepts periodontal probes, mirrors and percussive hammers. The patented invention lacks the forked end of the present invention which limits the patented invention to accepting a single interchangeable instrument on the forked end.

Numerous innovations for dental instruments have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a dental tool which has a handle on one end which has a smooth flat end, and a grip area. The opposite distal end of the handle is forked. A first tine of the fork is securely attached to a dental tool. The dental tool is selected from a group consisting of peritoneal probe, amalgam plugger, football burnisher, amalgam carver, currette and explorer. The second tine of the fork is securely attached to a support means for a mirror. The mirror may be rotatably attached to the tine and the second tine may be rotatably attached to the handle.

The types of problems encountered in the prior art are examining a patient teeth on the side away from the dentist. In the prior art both a mirror and a dental probe must be manipulated relative to each other while examining a patients teeth. This requires the dentist to use both hands.

In the prior art, both a mirror and a dental probe must be manipulated relative to each other while examining a patients teeth. This requires the dentist to use both hands. However, the problem was solved by the present invention because a mirror is attached to the dental probe and spaced apart to an operable position from the probe tip.

The present invention went contrary to the teaching of the art by incorporating the mirror and probe into a single instrument.

The present invention solved a long felt need for a dental probe which frees the user's hand.

Accordingly, it is an object of the present invention to provide a handle with a grip.

More particularly, it is an object of the present invention to provide dental probe having a probe first shaft attached to a probe second shaft which terminates in a probe point.

In keeping with these objects, and with others which will become apparent hereinafter, one feature of the present invention resides, briefly stated, in a mirror assembly which is rotatably attached to the handle.

When the dental tool is designed in accordance with the present invention the mirror can be positioned relative to the tip of the probe which enhances the dentist's ability to examine the patent's teeth.

The novel features which are considered characteristic for the invention are set froth in the appended claims. The invention itself, however, both as to its construction and its method of operation, together with additional objects and advantages thereof, will be best understood from the following description of the specific embodiments when read and understood in connection with the accompanying drawings.

LIST OF REFERENCE NUMERALS UTILIZED IN THE DRAWINGS

10 - dental instrument (10)

12 - handle (12)

12A - handle grip (12A)

12F - handle front (12F)

12R - handle rear (12R)

14 - probe (14)

14A - probe first shaft (14A)

14B - probe second shaft (14B)

14C - probe point (14C)

16 - mirror (16)

16A - mirror first shaft (16A)

16B - mirror second shaft (16B)

16C - mirror plate (16C)

DESCRIPTION OF THE PREFERRED EMBODIMENT

Figure 1:
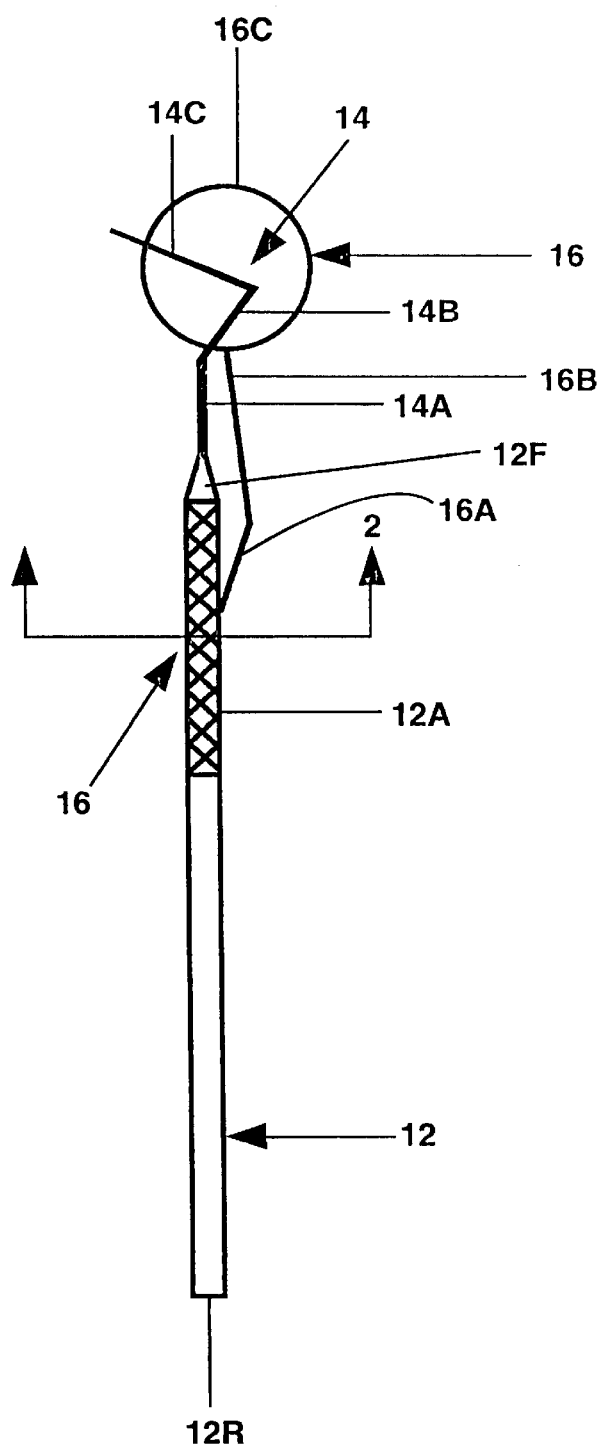
FIG. 1 is a side view of a dental instrument (10).

Firstly, referring to FIG. 1 which is a side view of a dental instrument (10). The dental instrument (10) comprises a handle (12) which comprises a handle front (12F) and a handle rear (12R). The handle (12) comprises a handle grip (12A) thereon.

The dental instrument (10) further comprises a probe (14) which is securely attached to and extending frontwardly from the handle front (12F). The probe (14) functions to measure periodontal pockets. The probe (14) comprises a probe first shaft (14A) which is securely connected at a rear distal end to a front distal end of the handle front (12F). The probe first shaft (14A) is in an approximately parallel configuration to a longitudinal axis of the handle (12). The probe (14) further comprises a probe second shaft (14B) which is securely connected at a rear distal end at an upward obtuse angle to a front distal end of the probe first shaft (14A). The probe (14) still further comprises a probe point (14C), having a rear distal end and a front distal end, which is securely connected at a rear distal end at an approximate perpendicular downward angle to a front distal end of the probe second shaft (14B). The probe point (14C) comprises indicia functioning to measure distance from the front distal end of the probe point (14C).

The dental instrument (10) still further comprises a mirror (16) which is securely attached to and extending frontwardly from the handle front (12F). The mirror (16) functions to allow a user to view the patient's teeth while measuring periodontal pockets. The mirror (16) comprises a mirror first shaft (16A) which is securely connected at a rear distal end to a front distal end of the handle front (12F). The mirror first shaft (16A) is in slightly upward obtuse angle to a longitudinal axis of the handle (12). The probe (14) further comprises a mirror second shaft (16B) which is securely connected at a rear distal end at an downward obtuse angle to a front distal end of the mirror first shaft (16A). The probe (14) further comprises a mirror plate (16C) which securely connected to a front distal end of the mirror second shaft (16B).

The dental instrument (10) is manufactured from a material selected from a group consisting of plastic, plastic composite, metal, metal alloy, wood, wood composite, glass, fiberglass, epoxy, carbon-graphite, rubber, and rubber composite.

Figure 2:
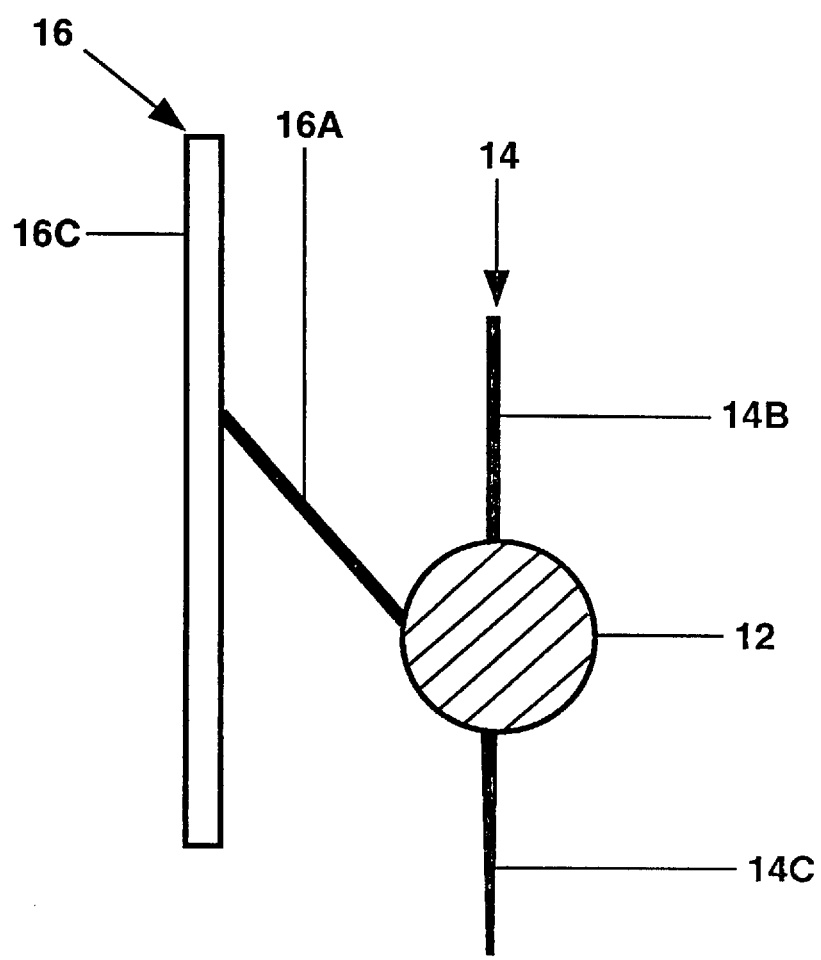
FIG. 2 is a rear view of a dental instrument (10) along line 2—2 of FIG. 1.

Lastly, referring to FIG. 2 which is a rear view of a dental instrument (10) along line 2—2 of FIG. 1. The dental instrument (10) comprises a handle (12). The dental instrument (10) further comprises a probe (14) which is securely attached to and extending frontwardly from the handle (12). The probe (14) functions to measure periodontal pockets. The probe (14) comprises a probe second shaft (14B) which is securely connected at a rear distal end at an upward obtuse angle to a front distal end of the probe first shaft (14A). The probe (14) still further comprises a probe point (14C) which is securely connected at a rear distal end at an approximate perpendicular downward angle to a front distal end of the probe second shaft (14B).

The dental instrument (10) still further comprises a mirror (16) which is securely attached to and extending frontwardly from the handle front (12F). The mirror (16) functions to allow a user to view the patient's teeth while measuring the depth of periodontal pockets. The mirror (16) comprises a mirror first shaft (16A) which is securely connected at a rear distal end to a front distal end of the handle front (12F). The mirror first shaft (16A) is in slightly upward obtuse angle to a longitudinal axis of the handle (12). The mirror (16) may be rotationally attached to the handle front (12F) permitting an adjustment of the mirror (16) relative to the handle front (12F). The probe (14) further comprises a mirror second shaft (16B) which is securely connected at a rear distal end at a downward obtuse angle to a front distal end of the mirror first shaft (16A). The probe (14) further comprises a mirror plate (16C). The mirror plate (16C) is reflective on at least the side facing the probe point (14C).

The dental instrument (10) is manufactured from a material selected from a group consisting of plastic, plastic composite, metal, metal alloy, wood, wood composite, glass, fiberglass, epoxy, carbon-graphite, rubber, and rubber composite.

It will be understood that each of the elements described above, or two or more together, may also find a useful application in other types of constructions differing from the type described above.

While the invention has been illustrated and described as embodied in a dental instrument, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A dental instrument (10) the dental instrument (10) comprising

A) a handle (12) which comprises a handle front (12F) and a handle rear (12R), the handle (12) comprises a handle grip (12A) thereon;

B) a probe (14) securely attached to and extending frontwardly from the handle front (12F) functioning to remove debris from a patient's teeth, the probe (14) comprises a probe first shaft (14A) securely connected at a rear distal end to a front distal end of the handle front (12F), the probe first shaft (14A) is in an approximately parallel configuration to a longitudinal axis of the handle (12), the probe (14) further comprises a probe second shaft (14B) securely connected at a rear distal end at an upward obtuse angle to a front distal end of the probe first shaft (14A), the probe (14) further comprises a probe point (14C) securely connected at a rear distal end at an approximate perpendicular downward angle to a front distal end of the probe second shaft (14B), the probe (14) is rotationally attached to and extends from the handle front (12F) functioning to permit adjustment of the mirror (16) relative to the probe point (14C); and C) a mirror (16) securely attached to and extending frontwardly from the handle front (12F) functioning to allow a user to view the patient's teeth while removing debris therefrom, the mirror (16) comprises a mirror first shaft (16A) securely connected at a rear distal end to a front distal end of the handle front (12F), the mirror first shaft (16A) is in slightly upward obtuse angle to a longitudinal axis of the handle (12), the probe (14) further comprises a mirror second shaft (16B) securely connected at a rear distal end at an downward obtuse angle to a front distal end of the mirror first shaft (16A), the probe (14) further comprises a mirror plate (16C) securely connected to a front distal end of the mirror second shaft (16B).

2. The dental instrument (10) as described in claim 1, wherein the probe point (14C) has a front distal end, the probe point (14C) has indicia imprinted thereon functioning to measure distance from the front distal end of the probe point (14C).

3. The dental instrument (10) as described in claim 1, wherein the probe (14) is selected from a group consisting of periodontal probe, amalgam plugger, football burnisher amalgam carver, currette and explorer.

4. The dental instrument (10) as described in claim 1 is manufactutred from a material selected from a group consisting of plastic, plastic composite, metal, metal alloy, wood, wood composite, fiberglass, epoxy, carbon-graphite, rubber, and rubber composite.

* * * * *